United States Patent
Grothe, Jr. et al.

(10) Patent No.: US 8,940,546 B2
(45) Date of Patent: Jan. 27, 2015

(54) METHOD FOR HIGHLY MULTIPLEXED QUANTITATION OF PEPTIDES BY MASS SPECTROMETRY AND MASS LABELS THEREFOR

(71) Applicants: Robert A. Grothe, Jr., Mountain View, CA (US); Justin Blethrow, Oakland, CA (US)

(72) Inventors: Robert A. Grothe, Jr., Mountain View, CA (US); Justin Blethrow, Oakland, CA (US)

(73) Assignee: Thermo Finnigan LLC, San Jose, CA (US)

( * ) Notice: Subject to any disclaimer, the term of this patent is extended or adjusted under 35 U.S.C. 154(b) by 0 days.

(21) Appl. No.: 14/000,856

(22) PCT Filed: May 9, 2013

(86) PCT No.: PCT/US2013/040402
§ 371 (c)(1),
(2) Date: Aug. 21, 2013

(87) PCT Pub. No.: WO2013/170067
PCT Pub. Date: Nov. 14, 2013

(65) Prior Publication Data
US 2014/0093968 A1    Apr. 3, 2014

Related U.S. Application Data

(60) Provisional application No. 61/645,311, filed on May 10, 2012.

(51) Int. Cl.
*G01N 27/62* (2006.01)
*G01N 30/72* (2006.01)
*G01N 33/68* (2006.01)

(52) U.S. Cl.
CPC ............. *G01N 27/62* (2013.01); *G01N 33/6848* (2013.01); *G01N 2458/15* (2013.01)
USPC .......................................... 436/173; 436/544

(58) Field of Classification Search
CPC .......... G01N 33/6848; G01N 2458/15; G01N 33/58; C07B 2200/05
See application file for complete search history.

(56) References Cited

PUBLICATIONS

Pichler et al. Peptide labeling with isobaric tags yields higher identificaiton rates using iTRAQ 4-plex compared to PMT 6-plex and iTRAQ on LTQ Orbitrap. Anal. Chem. 2010, vol. 82, pp. 6549-6558.*
Dayon et al., "Relative Quantification of Proteins in Human Cerebrospinal Fluids by MS/MS Using 6-Plex Isobaric Tags," Analytical Chemistry, 80 (8), 2008, pp. 2921-2931.
Atwood III et al, "Quantitation by Isobaric Labeling: Applications to Glycomics," Journal of Proteome Research 2008, 7, pp. 367-374.
Treumann et al., "Isobaric protein and peptide quantification: perspectives and issues," Expert Review of Proteomics, 7 (5), 2010, pp. 647-653.
Werner et al., "High-Resolution Enabled TMT 8-plexing," Analytical Chemistry 84 (16), 2012, pp. 7188-7194.
McAlister et al., "Increasing the Multiplexing Capacity of TMTs Using Reporter Ion Isotopologues with Isobaric Masses," Analytical Chemistry 84 (17), 2012, pp. 7469-7478.
PCT International Search Report and Written Opinion by the European Patent Office, mailed Jul. 29, 2013, pp. 1-11.

* cited by examiner

*Primary Examiner* — Shafiqul Haq
(74) *Attorney, Agent, or Firm* — Charles B. Katz

(57) ABSTRACT

Disclosed herein are isobaric labeling reagent sets useful for multiplexed quantitation of peptides. The isobaric labeling reagent sets include a collection of at least two isobaric labeling reagents having first and second reporter groups with the same nominal mass but different isotopic substitutions and consequently different exact masses. Mass spectrometric analysis of the labeled samples is performed using a mass analyzer, such as an Orbitrap mass analyzer, capable of adequately resolving the ions of the first and second reporter groups. Reagent sets of the foregoing description may provide a degree of multiplexing in reporter ion quantitation experiments that is expanded relative to conventional labeling reagent sets, thereby reducing the number of chromatographic runs required for analysis and improving sample throughput.

12 Claims, 3 Drawing Sheets

METHOD FOR HIGHLY MULTIPLEXED QUANTITATION OF PEPTIDES BY MASS SPECTROMETRY AND MASS LABELS THEREFOR

CROSS-REFERENCE TO RELATED APPLICATIONS

This application is a National Stage application under 35 U.S.C. §371 of PCT Application No. PCT/US2013/040402, filed May 9, 2013, which claims the priority benefit of U.S. Provisional Patent Application Ser. No. 61/645,311 for "Method for Highly Multiplexed Quantitation of Peptides by mass Spectrometry and Mass Labels Therefor", filed May 10, 2012, which applications are incorporated herein by reference in their entireties.

FIELD OF THE INVENTION

The present invention relates generally to methods for multiplexed quantitation of peptides by mass spectrometry utilizing isobaric mass labels, and more particularly to a set of isobaric mass labels useful for providing enhanced sample multiplexing capabilities and methods employing such sets of mass labels.

BACKGROUND OF THE INVENTION

Isobaric mass tagging or labeling is a method for determining the relative abundance of a given peptide across multiple samples by mass spectrometry. Each sample, typically representing a distinct biological condition, is reacted with a different isotopic variant of a labeling reagent. The samples are mixed together and analyzed by MS/MS. When a given peptide (isobaric molecules collected from all conditions) is isolated and fragmented, reporter ions arising from the various labeling reagents have different nominal masses, identifying the origin of each peptide, and allowing relative quantification of the peptide across samples. Sets of isobaric mass tagging reagents are commercially available from Thermo Fisher Scientific Inc, under the trade name Tandem Mass Tags (TMT), and from AB Sciex under the trade name Isobaric Tags for Relative and Absolute Quantitation (iTRAQ). The structure and utilization of isobaric mass tags has been described extensively in the patent prior art (see, for example, U.S. Pat. No. 7,816,304 by Schmidt et al. and U.S. Pat. No. 7,732,378 by Thompson et al., the disclosures of which are both incorporated herein by reference) as well as in the scientific literature (see, for example, Ross et al., "Multiplexed Protein Quantitation in *Saccharomyces cerevisiaie* Using Amine-reactive Isobaric Tagging Reagents", Molecular & Cellular Proteomics, 3(12), pp. 1154-1167 (2004); and, Dayon et al., "Relative Quantification of Proteins in Human Cerebrospinal Fluids by MS/MS Using 6-Plex Isobaric Tags", Analytical Chemistry, Vol. 80, pp. 2921-2931 (2008)).

Considerable effort has been invested in increasing the "multiplex" capacity of the isobaric mass tag system. For example, the "sixplex TMT" reagent set has additional value over the "fourplex iTRAQ" reagent set because it allows the user to compare more samples with fewer chromatographic runs. The multiplex capacity of the system is ultimately limited by the number of atoms in the reporter region of the isobaric reagent available for isotopic substitution and the difficulty and cost associated with introducing a large number of isotopic substitutions.

U.S. Patent Application Publication No. 2010/0029495 to Schaefer describes an approach to expanding multiplexing capacity by providing a set of labeling reagents which includes a plurality of reagents having reporter groups of the same mass but of different molecular structures. Its technique involves performing a second stage of fragmentation ($MS^3$) to cause fragmentation of the reporter ions, such that each same-mass reporter group yields characteristic product ions that may be distinguished in the mass spectrum, thereby permitting assignment of the relevant intensity to the corresponding labeled sample. While this approach may provide for a greater degree of multiplexing, the requirement of performing $MS^3$ to distinguish different reporter ions of the same mass complicates the analysis, and may reduce sensitivity and throughput.

SUMMARY

In accordance with embodiments of the present invention, a set of isobaric labeling reagents are provided wherein at least two of the labeling reagents have reporter groups with the same elemental composition and nominal (integer) mass but different isotopic substitutions and consequently different exact masses; for example, one reporter group may have one or more carbons substituted with the $^{13}C$ isotope, while the other reporter group may have a corresponding number of nitrogens substituted with the $^{15}N$ isotope (or a combination of $^{13}C$ and $^{15}N$ isotopes). The reporter ions produced by ionization and fragmentation of peptides labeled with these at least two reagents (i.e., during MS/MS analysis) have exact masses that are sufficiently different to enable them to be resolved from one another in a mass spectrum acquired using an Orbitrap, Fourier Transform/Ion Cyclotron Resonance (FT/ICR) or other instrument capable of high-resolution, accurate mass operation. The inclusion of two or more labeling reagents having reporter groups with the same nominal mass but different isotopic substitutions can significantly increase the multiplexing capability of a labeling reagent having a specified reporter group structure, thereby enabling a greater number of samples to be analyzed within a single chromatographic run and avoiding the uncertainties arising from run-to-run variations, which compromise the ability to directly compare data acquired for different samples. The increased multiplexing capability enabled by embodiments of the present invention also presents the advantage of increasing overall sample throughput, thus decreasing the amount of time required to complete an experiment and/or increasing the numbers of sample that may be analyzed within a given time.

The present invention also provides a method for highly multiplexed MS/MS analysis of a plurality of samples. In certain illustrative implementations, the samples may correspond to biological replicates, points in a time course, different cell lines, various perturbations of the biological system, etc. The method includes providing a set of isobaric labeling reagents, wherein at least two of the reagents have reporter groups that possess the same nominal mass and elemental composition but have different isotopic substitutions (as used herein, two reporter groups have different isotopic substitutions if one reporter group has a different number of one substituent, e.g., $^{13}C$ or $^{15}N$, relative to the other reporter group). Each one of the samples is reacted with a different reagent of the labeling reagent set to yield labeled analytes (e.g., molecules comprising a peptide of interest bound to a labeling reagent). The samples are then combined and subjected to MS/MS analysis, whereby the labeled analytes are (preferably) isolated and fragmented under controlled conditions, for example by collisionally activated dissociation (CAD). Product ions produced by dissociation of the labeled analytes include reporter ions, each having a characteristic mass. The mass analyzer is operated to acquire an MS/MS mass spectrum at a sufficiently high resolution to enable reporter ions of the same nominal mass but differing isotopic substitutions to be resolved as separate peaks. The relative quantities of the analyte(s) of interest may then be determined from the reporter ion intensities in the MS/MS spectrum, whereby each reporter ion peak corresponds to a different sample.

DETAILED DESCRIPTION OF ILLUSTRATIVE EMBODIMENTS

The invention is described below in reference to certain specific embodiments. It should be recognized that the embodiments described below are presented by way of illustration, and the invention should not be construed as being limited to the disclosed embodiments, but instead should be accorded the full scope of the claims presented below.

Figure 1:
FIG. 1 is a symbolic diagram depicting the component groups of a generic isobaric labeling reagent.

The structure and synthesis of isobaric labeling reagents are well-known in the art and need not be discussed in detail herein. Typically, an isobaric labeling reagent is formed from three linked groups or moieties, as depicted in FIG. 1, consisting of a reporter group, a mass normalizing group, and a reactive group. Each labeling reagent has a reporter group mass that is different from that of the other labeling reagents of the set (in conventional labeling reagent sets, the reporter groups have different nominal masses); the isobaric character of the labeling reagents is effected by providing a mass normalizing group having a mass that "balances out" the differential mass of the reporter group, such that all composite nominal masses are the same. The adjustment of reporter group and mass normalizing group masses is achieved by isotopic substitution, as described below. The reactive group reacts with the free amino-terminus of peptides to form a labeled analyte, which is ionized in a mass spectrometer, typically by the electrospray ionization technique. The reporter group is attached to the mass normalizing group by a cleavable linker, which fragments under CAD or equivalent conditions to release the reporter group, which retains charge and is thus observable in the product ion spectrum.

Figure 2:
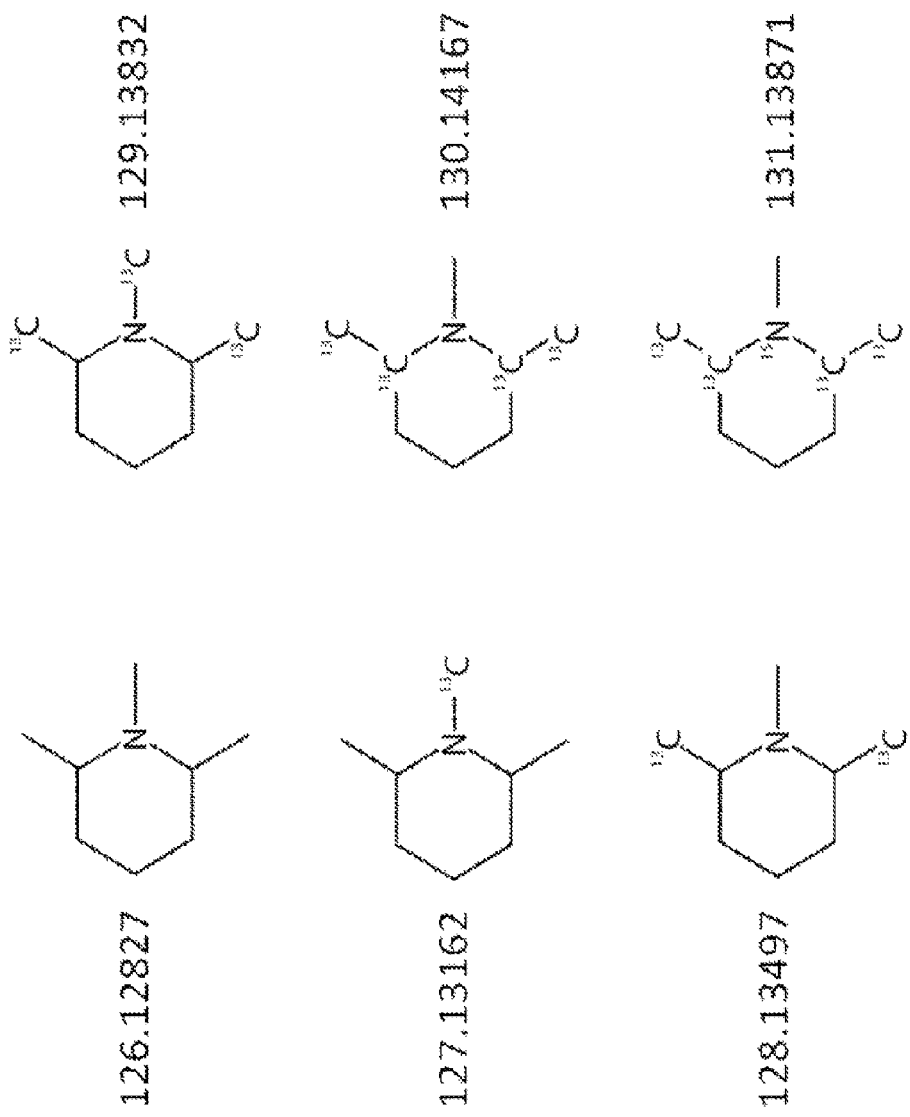
FIG. 2 depicts the isotopic variants of the members of the sixplex-TMT reagent set.

The current commercially available sixplex TMT system (referred to as "TMT-6" and sold by the Pierce Protein Biology Products business of Thermo Fisher Scientific Inc.) gives rise to six isotopic variants of the same reporter group $C_8H_{16}N$, as shown in FIG. 2. The six variants correspond to reporter groups with 0, 1, 2, 3, 4, and 5 additional neutrons, corresponding to nominal masses 126, 127, 128, 129, 130, and 131 respectively. When an extra neutron is placed on a carbon atom ($^{12}C \rightarrow ^{13}C$), the increase in mass (1.00335 Dalton (Da)) is slightly different than when it is placed on a nitrogen atom ($^{14}N \rightarrow ^{15}N$ 0.99703 Da). For example, the group with nominal mass 127 shown above is a $^{13}C$ substituted variant. Alternatively, a reporter group of nominal mass 127 could be formed by substituting $^{15}N$ instead of $^{13}C$. The $^{13}C$ form is 6.32 milliDalton (mDa) heavier than the $^{15}N$ form.

Given a mass spectrometry system that cannot accurately quantify a pair of ions closer than one mass unit apart, the set of isobaric labeling reagents will incorporate either the $^{13}C$ or $^{15}N$ substituted form of the reporter ion, but not both together. However, if a mass spectrometer is employed that is capable of accurately quantifying two species that have an exact mass difference of 6.32 mDa, it is possible to use both reporter ions (the $^{13}C$ and $^{15}N$ substituted forms) to encode sample information. Quantifying the reporter ions given in this example requires that the analyzer's "quantitative resolving power" exceed 20,000 (20K). We may define quantitative resolving power as m/dm, where dm is the smallest mass separation for which distinct ion species with masses m and m+dm can be accurately quantified. We observe that most commercial instruments require baseline separation of adjacent ions for accurate quantification. This means that the quantitative resolving power may be a factor of 2-5 times less than the resolution specification. Commercially available FTMS analyzers including the Orbitrap mass spectrometer and FT-ICR MS instruments are capable of far exceeding 100K in resolution, so that the quantitative resolving power clearly exceeds 20K. Certain time-of-flight (TOF) instruments also have resolution in excess of 20K, but it is unclear whether they have sufficient quantitative resolving power for the proposed application.

The quantitative resolving power of an Orbitrap or other Fourier Transform analyzer is known to be roughly proportional to the transient duration over which the mass spectrum is acquired, which is referred to herein as the scan time. Otherwise expressed, the scan time required to accurately quantify adjacent reporter ion peaks is inversely proportional to the exact mass difference between the adjacent reporter ion peaks (it is noted that in the context of discussion of mass spectrometric analysis, the term "mass" and its variants are used herein as shorthand for the measured mass-to charge ratio (m/z)). The inventors have demonstrated the ability to accurately quantify peaks having a 6.32 mDa exact mass difference in a commercially available Orbitrap instrument operated with a scan time of less than 32 milliseconds (ms). In this example, very high MS/MS scan rates, up to 30 Hz, would be possible, without losing the ability to resolve and accurately quantify the relative abundances of the reporter ions. As will be discussed below, accurate quantification of more closely spaced reporter ion peaks is feasible, but necessitates longer scan times and consequently lower scan rates. While commercially available versions of the Orbitrap analyzer are adequate to provide the required resolving power at acceptable scan rates, scan rates and throughput may be further increased by the use of data acquisition and processing techniques such as matched-filter linear deconvolution.

In accordance with embodiments of the present invention, the multiplexing capability of a isobaric reagent set having a given reporter group structure may be expanded by inclusion of reporter groups having the same elemental composition and nominal mass, but different numbers of $^{15}N$ and $^{13}C$ substitutions (and consequently different exact masses), and may be expanded still further by the inclusion of nominally isobaric reporter groups having different numbers of $^{15}N$, $^{13}C$ and $^2H$ substitutions. The table set forth below lists a total of 36 candidate reporter groups, each having the molecular structure utilized in the commercially available TMT-6 labeling reagents and having (except for the reporter ion having a nominal mass of 126) one or more isotopic substitutions. The table indicates, for each reporter group, the nominal and exact masses, the number of $^{15}$N, $^{13}$C and $^2$H substitutions, and the differential mass (designated as Δmass) representing the exact mass difference relative to the lower-mass adjacent reporter group within a collection of reporter groups having the same nominal mass (i.e., the reporter group appearing immediately above in the table). The reporter groups currently used for the TMT-6 set are marked as TMT-6 in the notes column. As indicated in the table, it is possible to select a set of 11 reporter groups, comprising the nominal mass 126 reporter group, plus a collection of two reporter groups each at nominal masses 127-131, with each of the reporter ions at nominal masses 127-131 representing zero or one $^{15}$N substitution combined with one or more $^{13}$C substitutions, with each reporter ion in the set being separated from adjacent reporter ions within the set by at least 6.3 mDa. As noted above, it is possible to quantify peaks having an accurate mass difference of 6.3 mDa with a mass analyzer having a nominal resolving power of 20K. The five additional (relative to the TMT-6 set) reporter groups are marked as "TMT-11" in the notes column of the table.

$^2$H substitutions can also be used to form a much larger set of reporter groups. Adding a neutron to $^1$H to form $^2$H increases its mass by 1.00628 Da. In principle, we could form (8+1)*(16+1)*(1+1)=306 different isotopic forms of $C_8H_{16}N$, representing all possible substitution patterns. However, if we restrict ourselves to substitutions of nominal masses 126-131 (analogous to the TMT-6 reagent set), there are 36 different isotopic forms. These 36 forms comprise the candidate reporter groups set forth in the table below.

Out of the total of 36 candidate reporter groups, a set comprised of thirty groups can be chosen so that all are separated by 2.93 mDa or greater; there are six pairs that separated by just 0.46 mDa. We selected one representative from each of these pairs for inclusion into a set of 30 reporter groups. The six isotopic forms eliminated from consideration are indicated as such in the table.

| Nominal Mass | Exact Mass | No. $^{15}$N | No. $^{13}$C | No. $^2$H | Δmass | Notes |
|---|---|---|---|---|---|---|
| 126 | 126.12827 | 0 | 0 | 0 | | TMT-6 |
| 127 | 127.1253 | 1 | 0 | 0 | | TMT-11 |
| 127 | 127.13162 | 0 | 1 | 0 | 0.00632 | TMT-6 |
| 127 | 127.13455 | 0 | 0 | 1 | 0.00293 | |
| 128 | 128.12865 | 1 | 1 | 0 | | TMT-11 |
| 128 | 128.13158 | 1 | 0 | 1 | 0.00293 | |
| 128 | 128.13497 | 0 | 2 | 0 | 0.00339 | TMT-6 |
| 128 | 128.1379 | 0 | 1 | 1 | 0.00293 | |
| 128 | 128.14083 | 0 | 0 | 2 | 0.00293 | |
| 129 | 129.132 | 1 | 2 | 0 | | TMT-11 |
| 129 | 129.13493 | 1 | 1 | 1 | 0.00293 | |
| 129 | 129.13786 | 1 | 0 | 2 | 0.00293 | Eliminated |
| 129 | 129.13832 | 0 | 3 | 0 | 0.00046 | TMT-6 |
| 129 | 129.14125 | 0 | 2 | 1 | 0.00293 | |
| 129 | 129.14418 | 0 | 1 | 2 | 0.00293 | |
| 129 | 129.14711 | 0 | 0 | 3 | 0.00293 | |
| 130 | 130.13535 | 1 | 3 | 0 | | TMT-11 |
| 130 | 130.13828 | 1 | 2 | 1 | 0.00293 | |
| 130 | 130.14121 | 1 | 1 | 2 | 0.00293 | Eliminated |
| 130 | 130.14167 | 0 | 4 | 0 | 0.00046 | TMT-6 |
| 130 | 130.14414 | 1 | 0 | 3 | 0.00247 | Eliminated |
| 130 | 130.1446 | 0 | 3 | 1 | 0.00046 | |
| 130 | 130.14753 | 0 | 2 | 2 | 0.00293 | |
| 130 | 130.15046 | 0 | 1 | 3 | 0.00293 | |
| 130 | 130.15339 | 0 | 0 | 4 | 0.00293 | |
| 131 | 131.1387 | 1 | 4 | 0 | | TMT-6 |
| 131 | 131.14163 | 1 | 3 | 1 | 0.00293 | |
| 131 | 131.14456 | 1 | 2 | 2 | 0.00293 | Eliminated |
| 131 | 131.14502 | 0 | 5 | 0 | 0.00046 | TMT-11 |
| 131 | 131.14749 | 1 | 1 | 3 | 0.00247 | Eliminated |
| 131 | 131.14795 | 0 | 4 | 1 | 0.00046 | |
| 131 | 131.15042 | 1 | 0 | 4 | 0.00247 | Eliminated |
| 131 | 131.15088 | 0 | 3 | 2 | 0.00046 | |
| 131 | 131.15381 | 0 | 2 | 3 | 0.00293 | |
| 131 | 131.15674 | 0 | 1 | 4 | 0.00293 | |
| 131 | 131.15967 | 0 | 0 | 5 | 0.00293 | |

A nominal quantitative resolving power of about 40K would be required to quantify reporter ions having a 2.93 mDa separation; for 0.46 mDa, the quantitative resolving power required is more than six times greater. This quantitative resolving power may be achievable in the Orbitrap analyzer, but the required transient duration (scan time) would be more than six times longer relative to a spectrum acquired at a resolving power of 40K. Doing so would significantly reduce scan rate (i.e., the number of mass spectra acquired per unit time), and thus operating the mass analyzer at the higher resolving power may not be an acceptable tradeoff to increase the multiplex capacity an additional 20% from 30 to 36. Peaks corresponding to the thirty remaining reporter ions (those not eliminated due to their mass proximities to adjacent reporter ions within a nominal mass group) may be adequately resolved in an Orbitrap mass analyzer operated with a scan time of about 64 ms. This is compatible with MS/MS scan rates up to 15 Hz.

It is possible that certain of the isotopic forms that comprise the 30-reporter group set listed in the table may be difficult to synthesize, and thus may not be realizable in a commercially practical manner. However, in any case, the use of labeling reagents having one or more reporter groups having the same nominal mass but different isotopic substitutions, combined with MS/MS analysis by mass spectrometers capable of sufficiently high resolution to resolve the nominally isobaric reporter ions as separately quantifiable peaks, makes possible much higher multiplex capacity than would be possible with unit resolution.

It should be understood that the present invention should not be construed as being limited to any particular reporter group structure. The reporter group structure discussed above (which is employed for the commercially available TMT-6 isobaric labeling reagent set, and has a molecular formula of $C_8H_{16}N$) is provided only by way of an illustrative example. The principle of the invention, in which multiplexing capacity is expanded by inclusion of labeling reagents having nominally isobaric reporter groups, may be applied to any number of reporter group structures. Examples of other reporter group structures that may be adapted for the present invention include those described in U.S. Pat. Nos. 7,294,456; 7,732,304; 7,816,304; and 7,825,069 as well as U.S. Patent Application Publication Nos. 2010/0178710; 2010/0029495; 2010/0167267; and 2011/0111513, the entire disclosures of which are incorporated herein by reference. Further, the newly demonstrated ability to accurately quantify isobars at high scan rates could motivate a redesign of the reporter region of the TMT reagent to provide even more isotopic combinations to further increase the multiplex capacity.

It should be further recognized that the highly multiplexed labeling reagent sets described herein do not require any special adaptation or modification to the mass-normalizing and peptide-reactive groups of the labeling reagents. More particularly, the isotopic substitutions on the mass-normalizing groups need only balance out the differences in the nominal masses between or among the reporter groups, rather than compensate for the differences in exact masses. It is noted that the labeled analytes may thus exhibit differences in their exact masses, but such differences will be sufficiently small so as to not have a substantial impact on either chromatographic retention times or the co-isolation of labeled analytes for MS/MS analysis.

Figure 3:
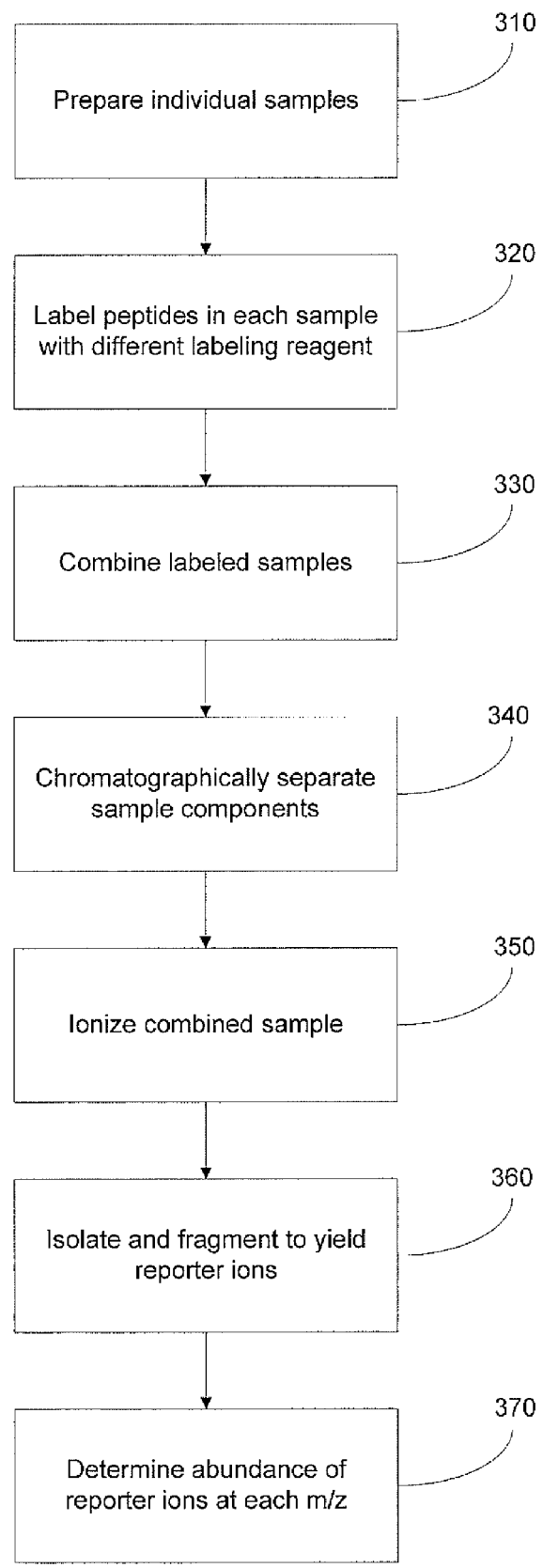
FIG. 3 is a diagram depicting a method for determining the relative abundance of a given peptide across multiple samples by mass spectrometry, using a isobaric labeling reagent set composed according to an embodiment of the invention.

Labeling reagent sets of the foregoing description may be utilized in substantially the same manner as commercially available labeling reagent sets, such as TMT-6. As depicted in FIG. 3, the analysis involves an initial step 310 of separately and identically preparing each one of a plurality of samples via known techniques suitable for purification and/or derivatization of analyte proteins and/or peptides present in the samples, which may include immunoaffinity capture/enrichment, denaturing, centrifugation/filtering, and proteolytic digestion. In a typical experiment, each sample may correspond to a different point of a time series with a corresponding one of the labeling reagents in order to form labeled analytes, e.g., peptides.

Next, each of the prepared samples is mixed with a different one of the labeling reagent of the isobaric reagent labeling set to produce labeled peptide analytes, for example via attachment of the labeling reagent to the amino terminal of peptides present in the sample, step 320. As discussed above, the isobaric reagent set will include a collection of at least two labeling reagents, in which the two labeling reagents have reporter groups having the same nominal masses but different isotopic substitutions; others of the labeling reagents will have reporter groups having different nominal masses. The prepared and labeled samples are then mixed together into a single combined sample, step 330. Off-line and/or on-line chromatographic separation techniques, for example strong cation exchange chromatography, may be utilized to separate components or groups of components from each other to simplify mass spectrometric analysis, per step 340. The combined sample (or chromatographic fractions thereof) is then subjected to MS/MS analysis employing a suitable mass spectrometer, such as the Thermo Scientific Q Exactive or Orbitrap Elite mass spectrometers. As known in the art, such analysis consists of first ionizing the sample mixture, step 350, which may be accomplished, for example, by electrospray ionization. The resultant ions are then mass selected (using, for example, a quadrupole mass filter or ion trap) to isolate one or more precursor ions of interest (i.e., those corresponding to a labeled peptide analyte), and fragmenting the precursor ions by CAD or other technique to generate product ions, step 360, which will include the reporter ions produced by fragmentation of the labeled analytes. In step 370, the abundances of reporter ions at each characteristic value of mass-to-charge ratio are determined by acquisition of a mass spectrum of the product ions produced in step 360. As discussed above, the product ion mass spectrum is acquired using a mass analyzer capable of and operated at a resolving power high enough to resolve the nominally isobaric reporter ions of differing isotopic composition. The mass analyzer may be, for example, an Orbitrap or FT/ICR analyzer. Per the foregoing example, a quantitative resolving power of 20K is adequate to resolve all reporter ions in the 11 reagent set identified in the table above (having a minimum separation between adjacent reporter ions of mDa), and a resolving power of 40K is adequate to resolve all ions in the 30 reagent set (having a minimum separation of 2.93 mDa). Each reporter ion peak in the spectrum is representative of and assignable to a different sample, and the relative quantities of an analyte of interest present in the samples may be determined from the relative intensities of the reporter ion peaks appearing at each characteristic m/z value, in the manner described in the art.

Various data processing methods known in the art may be utilized to increase the signal-to-noise ratio of the measured peaks and thereby improve the accuracy of the relative quantitation. Furthermore, the measured intensities may be adjusted (in accordance with known approaches, such as is described in U.S. Pat. No. 7,105,806 by Pappin et al.) to account for isotopic impurities in the labeling reagents, which result in the production of up-mass and down-mass side peaks.

What is claimed is:

1. A method of measuring the relative abundances of peptide analytes by mass spectrometry, comprising:
preparing a plurality of peptide-containing samples;
reacting each sample with an isobaric labeling reagent selected from an isobaric labeling reagent set to create differentially labeled peptides, the isobaric labeling reagent set consisting of a plurality of different isobaric labeling reagents wherein:
each isobaric labeling reagent comprises a reporter group, a mass normalizing group, a peptide-reactive group, and a cleavable linker attaching the reporter group to the mass normalizing group, each one of the plurality of isobaric labeling reagents having the same nominal mass;
each one of the isobaric labeling reagents has a reporter group with a mass different from the masses of the reporter groups of each of the other isobaric labeling reagents; and
a first collection of at least two of the isobaric labeling reagents have reporter groups of the same nominal mass but different exact mass by having different numbers of at least one of $^{13}C$, $^{15}N$ and $^{2}H$ substitutions;
wherein each sample is reacted with a unique one of the isobaric labeling reagents, such that labeled peptides in each sample have a reporter group mass that is different from the reporter group mass of the labeled peptides in each of the other samples, and wherein at least two of the samples are reacted with corresponding isobaric labeling reagents of the first collection;
combining the samples;
ionizing the combined samples to generate labeled peptide ions;
fragmenting the labeled peptide ions to produce reporter ions, the reporter ions having a mass-to-charge ratio uniquely characterizing one of the samples; and
measuring the abundances of the reporter ions at each characteristic mass-to-charge ratio using a mass analyzer.

2. The method of claim 1, wherein the mass analyzer is operable at a quantitative resolving power of at least 20K.

3. The method of claim 2, wherein the mass analyzer comprises an Orbitrap mass analyzer.

4. The method of claim 1, wherein the step of fragmenting the labeled peptide ions includes subjecting the labeled peptide ions to collisionally activated dissociation (CAD).

5. The method of claim 1, wherein the step of preparing the plurality of peptide-containing samples includes proteolytically digesting each sample.

6. The method of claim 1, further including a step of chromatographically separating the combined samples by chromatography.

7. The method of claim 1, wherein the first collection includes isobaric labeling reagents having reporter groups with different numbers of $^{13}C$ substitutions.

8. The method of claim 1, wherein the first collection includes isobaric labeling reagents having reporter groups with different numbers of $^{15}N$ substitutions.

9. The method of claim 1, wherein the first collection includes isobaric labeling reagents having reporter groups with different numbers of $^{2}H$ substitutions.

10. The method of claim 1, wherein the masses of reporter groups of the isobaric labeling reagents in the first collection differ from each other by at least 2.93 mDa.

11. The method of claim 1, wherein a second collection of at least two of the isobaric labeling reagents have reporter groups of the same nominal mass but different exact mass by having different numbers of at least one of $^{13}C$, $^{15}N$ and $^{2}H$ substitutions, the nominal mass of the reporter groups of the second collection being different from the nominal mass of the reporter groups of the first collection, and wherein at least two of the samples are reacted with corresponding isobaric labeling reagents of the second collection.

12. The method of claim 1, wherein the reporter groups of each of the plurality of isobaric labeling reagents have the structure:

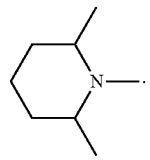

* * * * *